US012203945B2

(12) United States Patent
Taira et al.

(10) Patent No.: US 12,203,945 B2
(45) Date of Patent: Jan. 21, 2025

(54) HAEMOGLOBIN ANALYSIS METHOD FOR DETECTING ABNORMAL HAEMOGLOBINS AND/OR THALASSEMIA MARKERS (71) Applicant: SEKISUI MEDICAL CO., LTD., Chuo-ku (JP)

(72) Inventors: Hiroaki Taira, Chuo-ku (JP); Ei-Ichiro Sunamura, Chuo-ku (JP); Kohei Matsuda, Chuo-ku (JP); Takuya Yotani, Chuo-ku (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 511 days.

(21) Appl. No.: 16/971,393

(22) PCT Filed: Apr. 18, 2019

(86) PCT No.: PCT/JP2019/016633
§ 371 (c)(1),
(2) Date: Aug. 20, 2020

(87) PCT Pub. No.: WO2019/203302
PCT Pub. Date: Oct. 24, 2019

(65) Prior Publication Data
US 2020/0393472 A1 Dec. 17, 2020

(30) Foreign Application Priority Data

Apr. 18, 2018 (JP) .................... 2018-079937

(51) Int. Cl.
*G01N 33/72* (2006.01)
*G01N 30/02* (2006.01)
*G01N 30/34* (2006.01)
*G01N 30/88* (2006.01)
*G01N 30/96* (2006.01)

(52) U.S. Cl.
CPC ........... *G01N 33/721* (2013.01); *G01N 30/02* (2013.01); *G01N 30/96* (2013.01)

(58) Field of Classification Search
CPC ...... G01N 30/96; G01N 30/02; G01N 33/721; G01N 30/88; G01N 30/34
USPC .......................................................... 436/66
See application file for complete search history.

(56) References Cited

U.S. PATENT DOCUMENTS

| | | | | |
|---|---|---|---|---|
| 3,763,136 A * | 10/1973 | Huber | ................... | C12N 9/0089 530/416 |
| 3,763,137 A * | 10/1973 | Huber | ................... | C12N 9/0089 530/416 |
| 4,108,603 A * | 8/1978 | Regnier | ................. | B01J 20/289 436/66 |
| 4,246,084 A * | 1/1981 | Gurske | ................... | C12Q 1/007 435/26 |
| 4,407,961 A * | 10/1983 | Sanders | ............... | G01N 33/723 436/178 |
| 4,517,241 A * | 5/1985 | Alpert | ...................... | C12N 9/00 428/407 |
| 4,970,171 A * | 11/1990 | Messenger | ........... | G01N 33/723 436/66 |
| 5,260,419 A * | 11/1993 | Hayman | ............ | C07K 14/8132 530/416 |
| 5,294,336 A * | 3/1994 | Mizuno | ................ | G01N 33/723 210/198.2 |
| 5,296,465 A * | 3/1994 | Rausch | ................ | C07K 14/805 514/15.3 |
| 5,358,639 A * | 10/1994 | Yasuda | ................... | G01N 30/52 436/66 |
| 5,362,855 A * | 11/1994 | Garlick | ................ | C07K 14/805 530/385 |
| 5,439,591 A * | 8/1995 | Pliura | .................. | C07K 14/805 530/416 |
| 5,691,453 A * | 11/1997 | Wertz | ....................... | A61P 7/08 530/414 |
| 5,719,053 A * | 2/1998 | Noffsinger | ............. | G01N 30/88 436/66 |
| 5,753,465 A * | 5/1998 | Ho | ....................... | C07K 14/805 435/69.6 |
| 5,801,053 A | 9/1998 | Noffsinger et al. | | |
| 5,843,888 A * | 12/1998 | Ho | ....................... | C07K 14/805 530/385 |
| 6,150,506 A * | 11/2000 | Trimble | ............. | A61K 47/6445 530/361 |
| 6,150,507 A | 11/2000 | Houtchens et al. | | |
| 6,428,704 B1 * | 8/2002 | Setoguchi | .............. | G01N 30/96 436/66 |

(Continued)

FOREIGN PATENT DOCUMENTS

| | | |
|---|---|---|
| CN | 101198350 A | 6/2008 |
| CN | 102893147 A | 1/2013 |

(Continued)

OTHER PUBLICATIONS

Duchon, G. et al., Journal of Membrane Biology 1971, 6, 138-157.*
Jongeneel, J. et al., Clinical Chemistry 1979 25, 642.*
Seaman, C. et al., American Journal of Hematology 1980, 8, 31-42.*
Acharya, A. S. et al., Journal of Biological Chemistry 1980, 255, 1406-1412.*
Hall, L. A. et al., Journal of Chromatography 1983, 266, 409-425.*
Castagnola, M. et al., Journal of Chromatography 1983, 272, 51-65.*
Bisse, E. et al., Journal of Chromatography 1985, 344, 81-91.*
Nguyen, L. B. et al., Proceedings of the Society for Experimental Biology and Medicine 1986, 181, 151-156.*

(Continued)

*Primary Examiner* — Arlen Soderquist
(74) *Attorney, Agent, or Firm* — Oblon, McClelland, Maier & Neustadt, L.L.P.

(57) ABSTRACT

Provided is a method for separating and detecting various hemoglobins including abnormal hemoglobins and thalassemia markers. A method for analyzing hemoglobins, comprising separating hemoglobins in a sample by cation exchange chromatography, wherein an eluent having a pH of 8.1 or more and an osmotic pressure of 40 mOsm/kg or less is used for separation of the hemoglobins.

10 Claims, 7 Drawing Sheets

(56) References Cited

U.S. PATENT DOCUMENTS

| | | | | |
|---|---|---|---|---|
| 6,488,857 | B1* | 12/2002 | Shimada | B01D 15/362 436/66 |
| 6,828,125 | B1* | 12/2004 | Hoffman | A61K 47/6445 435/69.6 |
| 2003/0146161 | A1* | 8/2003 | Herman | B01D 15/18 210/657 |
| 2005/0064554 | A1* | 3/2005 | Fisher | A61P 19/10 514/4.8 |
| 2006/0102478 | A1 | 5/2006 | Robert et al. | |
| 2006/0292696 | A1* | 12/2006 | Noffsinger | G01N 33/96 436/66 |
| 2010/0209532 | A1* | 8/2010 | Dube | B01D 61/18 424/606 |
| 2013/0130391 | A1 | 5/2013 | Taira et al. | |
| 2013/0199277 | A1 | 8/2013 | Taira et al. | |
| 2015/0204889 | A1 | 6/2015 | Taira et al. | |
| 2015/0377846 | A1 | 12/2015 | Ishikawa et al. | |
| 2019/0300929 | A1* | 10/2019 | Ichiyanagi | C09B 67/0083 |
| 2019/0316174 | A1* | 10/2019 | Ichiyanagi | C07C 309/49 |

FOREIGN PATENT DOCUMENTS

| | | | |
|---|---|---|---|
| EP | 2 533 043 A1 | | 12/2012 |
| EP | 2 960 648 A1 | | 12/2015 |
| JP | 05113440 A | * | 5/1993 |
| JP | 10-227780 A | | 8/1998 |
| JP | 11-295286 A | | 10/1999 |
| JP | 11-304782 | * | 11/1999 |
| JP | 2001-21555 | * | 1/2001 |
| JP | 2001-221788 A | | 8/2001 |
| JP | 2002-520338 A | | 7/2002 |
| JP | 2003014714 A | * | 1/2003 |
| JP | 2010-237110 A | | 10/2010 |
| JP | 2012-168054 A | | 9/2012 |
| JP | 2012-168055 A | | 9/2012 |
| JP | 2016-27326 A | | 2/2016 |
| WO | 99/04269 | * | 1/1999 |
| WO | WO 2011/096420 A1 | | 8/2011 |
| WO | WO 2011/125484 A1 | | 10/2011 |

OTHER PUBLICATIONS

Esser, R. S. et al., Journal of Automatic Chemistry 1987, 9, 92-96.*
Christensen, S. M. et al., Journal of Biochemical and Biophysical Methods 1988, 17, 143-154.*
Zade-Oppen, A. M. M. et al., Journal of Membrane Biology 1990, 118, 143-151.*
Esser, R. S. et al., Biomedical Chromatography 1991, 5, 226-228.*
Slais, K. et al., Chromatographia 1992, 33, 231-236.*
Ou, C.-N. et al., Clinical Chemistry 1993, 39, 820-824.*
Brunnekreeft, J. W. et al., Clinical Chemistry 1993, 39, 2514-2518.*
Winslow, R. M. et al., Methodes in Enymology 1994, 231, 3-16.*
Itala, L. et al., Analytical Biochemistry 1995, 224, 323-329.*
Ou, C.-N., Journal of Biomedical Science 1997, 4, 315-318.*
Deepthi, S. et al., Biochimica et Biophysica Acta 2000, 1480, 384-387.*
Kang, X. et al., Journal of Chromatography A 2003, 991, 117-128.*
Manjula, B. N. et al., in "Methods in Molecular Medicine" 2003, 82, Nagel, R. L. ed, Humana Press Inc., Totowa, NJ, 31-47.*
Stanton, P. in "Methods in Molecular Biology" 2004, 251, Aguilar, M.-I. ed, Humana Press Inc., Totowa, NJ. 23-43.*
Dodge, J. T. et al., Archives of Biochemistry and Biophysics 1963, 100, 119-130. (Year: 1963).*
Weed, R. I. et al., Journal of Clinical Investigation 1963, 42, 581-588. (Year: 1963).*
Jacob, H. S. et al., Journal of Clinical Investigation 1971, 50, 1800-1805. (Year: 1971).*
Drousiotou, C. P. et al., Biochemical Society Transactions 1980, 8, 551. (Year: 1980).*
Buckley, J. T. et al., Biochemistry 1995, 34, 16450-16455. (Year: 1995).*
Brand, G. D. et al., Biochemical and Biophysical Research Communications 2006, 347, 739-746. (Year: 2006).*
Nielso, L. K. et al., Transfusion 2007, 47, 306-315. (Year: 2007).*
Zhou, Y. et al., Scientific Reports 2016, 6, paper 20136, 15 pages. (Year: 2016).*
Mitchell, C. D. et al., Biochimica et Biophysica Acta 1965, 104, 348-358. (Year: 1965).*
Prestidge, R. L. et al., Analytical Biochemistry 1979, 97, 95-102. (Year: 1979).*
Davio, S. R. et al., Bioch imica et Biophysica Acta 1981, 644, 157-164. (Year: 1981).*
Raval, P. J. et al., Bioch imica et Biophysica Acta 1989, 983, 230-240. (Year: 1989).*
Currivan, S. et al., Journal of Separation Science 2010, 33, 484-492. (Year: 2010).*
Extended European Search Report issued Dec. 16, 2021 in European Patent Application No. 19788856.3, 8 pages.
International Search Report issued on Jul. 23, 2019 in PCT/JP2019/016633 filed on Apr. 18, 2019, 2 pages.
Office Action issued on Aug. 1, 2023 in corresponding Chinese Application No. 201980026091.7, (with English Machine Translation).
Beverly Barton Rogers, M.D. et al., "High-performance Liquid Chromatography in the Diagnosis of Hemoglobinopathies and Thalassemias", American Journal of Clinical Pathology, vol. 84, No. 5, Nov. 30, 1985, pp. 671-674.
Office Action issued on Nov. 23, 2023 in corresponding Chinese Patent Application No. 201980026091.7 (with English Machine Translation) and (with machine translation).

* cited by examiner

HAEMOGLOBIN ANALYSIS METHOD FOR DETECTING ABNORMAL HAEMOGLOBINS AND/OR THALASSEMIA MARKERS

FIELD OF THE INVENTION

The present invention relates to a hemoglobin analysis method.

BACKGROUND ART

Hemoglobin (Hb) is a chromoprotein consisting of heme (pigment portion) that binds to oxygen and globin that carries the heme, and is involved in the transport of oxygen to cells throughout the body. The polypeptide of normal human globin has four subunits called $\alpha$, $\beta$, $\gamma$, and $\delta$ chains, and these constitute tetramers consisting of two $\alpha$ chains and two non-$\alpha$ chains. There are three tetramers present in normal human Hb: HbA ($\alpha 2\beta 2$), HbA2 ($\alpha 2\delta 2$) and HbF ($\alpha 2\gamma 2$), but HbA is the most common. HbA mainly includes HbA0 and glycated HbA1c, and HbA1c is used as a marker for diabetes and the like.

Abnormal globin subunit conformation causes hemoglobinopathy, whereas poor formation of globin subunits causes thalassemia, all of which result in anemia and, in more severe cases, hemolysis, underdevelopment, bone deformity, and the like. Hemoglobinopathy is generally diagnosed by detecting abnormal Hb such as HbS, HbC, HbE, and HbD. Thalassemia is classified broadly into $\alpha$ thalassemia due to poor formation of $\alpha$ chains and $\beta$ thalassemia due to poor formation of $\beta$ chains, and is generally diagnosed using high values of HbA2, HbF, and the like as an index.

There are methods for detecting abnormalities in hemoglobin using high performance liquid chromatography (HPLC). Patent Literature 1 describes that it is possible to separate HbS, HbC, HbE and HbD, which are abnormal Hb, and thalassemia markers HbA2 and HbF, by HPLC using a gradient elution in which a plurality of eluents containing a phosphoric acid monohydrogen dialkali metal salt (component 1) and a phosphoric acid dihydrogen monoalkali metal salt (component 2) at different ratios are sequentially fed. Patent Literature 2 describes that HbA0, HbS and HbC were separated by ion exchange liquid chromatography using an eluent containing an ion pair reagent and having a pH in the range of 7.1 to 7.3. Patent Literature 3 describes a method for analyzing hemoglobin S using an eluent having a pH of 6.88 to 7.50, or hemoglobin A2 using an eluent having a pH of 6.60 to 6.80 by cation exchange high performance liquid chromatography.

CITATION LIST

Patent Literature

Patent Literature 1: JP-A-2016-27326
Patent Literature 2: JP-A-2010-237110
Patent Literature 3: WO 2011/096420

SUMMARY OF THE INVENTION

Problem to be Solved by the Invention

The present invention relates to a method for separating and detecting various hemoglobins including abnormal hemoglobins and thalassemia markers from a blood sample.

Means for Solving the Problem

Accordingly, the present invention provides the following.

[1] A method for analyzing hemoglobins, comprising separating hemoglobins in a sample by cation exchange chromatography,
wherein an eluent having a pH of 8.1 or more and an osmotic pressure of 40 mOsm/kg or less is used for separation of the hemoglobins.

[2] The method according to [1], wherein the eluent comprises a buffer without metal ions.

[3] The method according to [2], wherein the buffer is Bicine, Tricine or TES.

[4] The method according to [2] or [3], wherein a concentration of the buffer in the eluent is 2 to 17 mmol/L.

[5] The method according to any one of [1] to [4], wherein the eluent comprises a hemoglobin denaturing agent.

[6] The method according to any one of [1] to [5], wherein the hemoglobins are separated by gradient elution using the eluent.

[7] The method according to [6], wherein a proportion of the eluent in the gradient increases from 0% to 100%.

[8] The method according to any one of [1] to [7], wherein at least one abnormal hemoglobin selected from the group consisting of HbS, HbC, HbE, HbD, and HbO-Arab is separated.

[9] The method according to any one of [1] to [8], wherein at least one thalassemia marker selected from the group consisting of HbA2, HbF, HbH, Hb Bart', and Hb Constant Spring is separated.

[10] The method according to any one of [1] to [9], wherein the chromatography is high performance liquid chromatography.

[11] An eluent for separating hemoglobins by cation exchange chromatography, wherein the eluent has a pH of 8.1 or more and an osmotic pressure of 40 mOsm/kg or less.

[12] The eluent according to [11], wherein the eluent comprises a buffer without metal ions.

[13] The eluent according to [12], wherein the buffer is Bicine, Tricine or TES.

[14] The eluent according to [12] or [13], wherein a concentration of the buffer in the eluent is 2 to 17 mmol/L.

[15] The eluent according to any one of [11] to [14], wherein the eluent comprises a hemoglobin denaturing agent.

[16] Use of a liquid composition having a pH of 8.1 or more and an osmotic pressure of 40 mOsm/kg or less as an eluent for separating hemoglobins by cation exchange chromatography.

[17] Use of a liquid composition having a pH of 8.1 or more and an osmotic pressure of 40 mOsm/kg or less for producing an eluent for separating hemoglobins by cation exchange chromatography.

[18] The use according to [16] or [17], wherein the liquid composition comprises a buffer without metal ions.

[19] The use according to [18], wherein the buffer is Bicine, Tricine or TES.

[20] The use according to [18] or [19], wherein a concentration of the buffer in the liquid composition is 2 to 17 mmol/L.

[21] The use according to any one of [16] to [20], wherein the liquid composition comprises a hemoglobin denaturing agent.

Effects of the Invention

According to the present invention, in addition to HbA0, which is the main hemoglobin, HbA1c, abnormal Hb, thalassemia markers, and the like, can be rapidly and highly sensitively separated from a blood sample. The present invention is useful for the simple, rapid and highly sensitive diagnosis of hemoglobinopathy or thalassemia.

DESCRIPTION OF THE EMBODIMENTS

All patent literatures, non-patent literatures, and other publications cited herein are incorporated by reference in their entirety.

The hemoglobin analysis method of the present invention comprises separating hemoglobins in a sample by ion exchange chromatography. As a sample to be used in the method of the present invention, a blood sample containing hemoglobins used for normal hemoglobin analysis can be used. For example, a blood sample obtained by hemolyzing or diluting blood collected from a human can be used.

The chromatography performed in the method of the present invention is preferably liquid chromatography, more preferably high performance liquid chromatography (HPLC). The ion exchange chromatography in the present invention can be performed using a known liquid chromatography system, that is, an ion exchange column connected to a system including a pump for eluent feeding, a sampler, a detector, and the like.

Preferably, the ion exchange chromatography performed in the method of the present invention is cation exchange chromatography using a cation exchange column. The cation exchange column used in the method of the present invention may be a column packed with a stationary phase having a cation exchange group. Examples of the cation exchange group include a carboxyl group, a phosphoric acid group, and a sulfonic acid group, among which a sulfonic acid group is preferable.

Examples of the stationary phase of the cation exchange column include filler particles and a porous body, with the filler particles being preferable. Examples of the filler particles include inorganic particles and organic particles. Examples of the inorganic particles include particles composed of silica, zirconia, and the like. Examples of the organic particles include natural polymer particles such as cellulose, polyamino acid, and chitosan, and synthetic polymer particles such as polystyrene and polyacrylic ester. Preferable examples of the stationary phase having a cation exchange group include a filler containing crosslinked polymer particles obtained by polymerizing a mixture of a non-crosslinkable hydrophilic acrylic monomers and polyglycidyl ethers, and a layer of an acrylic monomer having a cation exchange group polymerized on the surface of the crosslinked polymer particles, as disclosed in JP-A-2011-047858.

In the hemoglobin analysis method of the present invention, as in the conventional hemoglobin analysis by ion exchange chromatography, hemoglobins in a sample are adsorbed onto an ion exchange column, and then an eluent is passed through the column to elute the hemoglobins from the column, thereby separating the hemoglobins in the sample. Therefore, the eluent used in the hemoglobin analysis method of the present invention is an eluent used for separating hemoglobins by ion exchange chromatography. More preferably, the eluent is an eluent used for the elution of hemoglobins from a cation exchange column in cation exchange chromatography.

In the hemoglobin analysis method of the present invention, an eluent having a higher pH and a lower osmotic pressure than in the conventional hemoglobin analysis method is used. The eluent used in the present invention preferably has a pH of 8.1 or more. More specifically, the pH of the eluent is preferably 8.1 or more, more preferably 8.2 or more, further preferably 8.3 or more, while preferably 10.0 or less, more preferably 9.0 or less and further preferably 8.6 or less. If the eluent has a pH of less than 8.1, the elution of hemoglobin, particularly HbC, from the column may be insufficient, whereas if the pH exceeds 10, the separation of HbS and HbC in particular may be insufficient. Examples of the pH range of the eluent used in the present invention include pH 8.1 to 10.0, pH 8.1 to 9.0, pH 8.1 to 8.6, pH 8.2 to 10.0, pH 8.2 to 9.0, pH 8.2 to 8.6, pH 8.3 to 10.0, pH 8.3 to 9.0, and pH 8.3 to 8.6. In contrast, the pH of the eluent used in the conventional hemoglobin analysis method is usually about pH 5.0 to 8.0.

The osmotic pressure of the eluent used in the present invention is preferably 40 mOsm/kg or less. More specifically, the osmotic pressure of the eluent is preferably 40 mOsm/kg or less, more preferably 37 mOsm/kg or less, further preferably 36 mOsm/kg or less, while preferably 15 mOsm/kg or more, more preferably 19 mOsm/kg or more, further preferably 26 mOsm/kg or more. If the osmotic pressure of the eluent is less than 15 mOsm/kg, the elution of hemoglobin, particularly HbA0 and HbA2, may be insufficient, whereas if the osmotic pressure exceeds 40 mOsm/kg, the separation between hemoglobins, particularly HbA0 and HbA2, is poor. Examples of the range of the osmotic pressure of the eluent used in the present invention include 15 to 40 mOsm/kg, 15 to 37 mOsm/kg, 15 to 36 mOsm/kg, 19 to 40 mOsm/kg, 19 to 37 mOsm/kg, 19 to 36 mOsm/kg, 26 to 40 mOsm/kg, 26 to 37 mOsm/kg, and 26 to 36 mOsm/kg. In contrast, in the conventional hemoglobin separation by chromatography, the composition of the eluent is not designed from the viewpoint of osmotic pressure adjustment, and the osmotic pressure of the eluent conventionally used is usually about 125 to 570 mOsm/kg. The value of the osmotic pressure in the present specification refers to the value of the osmotic pressure measured by cryoscopy. The osmotic pressure can be measured using a commercially available osmometer, for example, Osmometer 3250 (manufactured by Advanced Instruments), and the like. Moreover, in the present specification, the unit of osmotic pressure, mOsm/kg, means mOsm/kg $H_2O$, which may also be expressed as mOsm/L or mOsm.

In order to prepare an eluent having the above pH and osmotic pressure ranges, in the present invention, the eluent contains a buffer without metal ions. Since the buffer solutions generally used in a conventional eluent, such as a phosphate buffer solution, contain metal ions, it is difficult to simultaneously achieve high pH and low osmotic pressure. Examples of the buffer without metal ions include Good's buffers, among which Bicine (N,N-bis(2-hydroxyethyl)glycine), Tricine (N-[tris(hydroxymethyl)methyl)glycine) or TES (N-tris(hydroxymethyl)methyl-2-aminoethanesulfonic acid) is preferable, and TES is more preferable.

The concentration of the above-mentioned buffer in the eluent used in the present invention may be a concentration that can adjust the pH and osmotic pressure of the final eluent to the above ranges, while taking into account the effects of the additives and the like described below. The concentration of the buffer in the eluent is preferably 2 mmol/L or more, more preferably 2.5 mmol/L or more, further preferably 5 mmol/L or more, while preferably 17 mmol/L or less, more preferably 15 mmol/L or less, further preferably 12.5 mmol/L or less. Examples of the range of the concentration of the buffer in the eluent used in the present invention include 2 to 17 mmol/L, 2 to 15 mmol/L, 2 to 12.5 mmol/L, 2.5 to 17 mmol/L, 2.5 to 15 mmol/L, 2.5 to 12.5 mmol/L, 5 to 17 mmol/L, 5 to 15 mmol/L, and 5 to 12.5 mmol/L.

Preferably, the eluent used in the present invention is a liquid composition in a state of solution containing Bicine, Tricine or TES as a buffer. The concentration of the buffer in the eluent is 2 to 17 mmol/L, and the eluent has an osmotic pressure of 15 to 40 mOsm/kg and a pH of preferably 8.1 to 10.0, more preferably 8.2 to 9.0, further preferably 8.2 to 8.6, and furthermore preferably 8.3 to 8.6.

More preferably, the eluent used in the present invention contains Bicine, Tricine or TES as a buffer, the concentration of the buffer in the eluent is 2.5 to 15 mmol/L, and the eluent has an osmotic pressure of 15 to 37 mOsm/kg and a pH of preferably 8.1 to 10.0, more preferably 8.2 to 9.0, further preferably 8.2 to 8.6, and furthermore preferably 8.3 to 8.6.

Further preferably, the eluent used in the present invention contains Bicine, Tricine or TES as a buffer, the concentration of the buffer in the eluent is 5 to 15 mmol/L, and the eluent has an osmotic pressure of 19 to 37 mOsm/kg and a pH of preferably 8.1 to 10.0, more preferably 8.2 to 9.0, further preferably 8.2 to 8.6, and furthermore preferably 8.3 to 8.6.

Furthermore preferably, the eluent used in the present invention contains Bicine, Tricine or TES as a buffer, the concentration of the buffer in the eluent is 5 to 15 mmol/L, and the eluent has an osmotic pressure of 26 to 36 mOsm/kg and a pH of preferably 8.2 to 9.0, further preferably 8.2 to 8.6, and furthermore preferably 8.3 to 8.6.

Furthermore preferably, the eluent used in the present invention contains Bicine, Tricine or TES as a buffer, the concentration of the buffer in the eluent is 5 to 12.5 mmol/L, and the eluent has an osmotic pressure of 26 to 36 mOsm/kg and a pH of 8.3 to 8.6.

The eluent used in the present invention may contain, in addition to the buffer described above, a solvent and additives such as a hemoglobin denaturing agent, a binding agent to trivalent heme iron, a pH adjuster, and a surfactant.

Preferably, the eluent used in the present invention contains a hemoglobin denaturing agent. The hemoglobin denaturing agent may be an oxidizing agent that can change the heme iron of hemoglobin from divalent to trivalent to generate methemoglobin. Examples of such oxidizing agent include nitrite salts, potassium ferricyanide, methylene blue, hydrogen peroxide, ascorbic acid, and hydrogen sulfide. Among these, nitrite salts are preferable, and sodium nitrite or potassium nitrite is more preferable. The concentration of the hemoglobin denaturing agent in the eluent is preferably 0.05 to 15 mmol/L, more preferably 1.0 to 10 mmol/L.

Preferably, the eluent used in the present invention contains a binding agent to trivalent heme iron. The binding agent to trivalent heme iron stabilizes the methemoglobin produced by the hemoglobin denaturing agent and stabilizes its elution behavior. Examples of the binding agent to trivalent heme iron include azides and cyanides. Examples of azides include sodium azide, diphenylphosphoryl azide, 4-dodecylbenzenesulfonyl azide, 4-acetylaminobenzenesulfonyl azide, potassium azide, lithium azide, iron azide, hydrogen azide, lead azide, mercury azide, copper azide, and silver azide. Examples of cyanides include potassium cyanide, hydrogen cyanide, sodium cyanide, silver cyanide, mercury cyanide, copper cyanide, lead cyanide, iron cyanide, lithium cyanide, and ammonium cyanide. Preferably, the binding agent to trivalent heme iron is an azide, more preferably sodium azide. The concentration of the binding agent to trivalent heme iron in the eluent is preferably 0.05 to 15 mmol/L, more preferably 0.5 to 10 mmol/L.

Examples of the pH adjuster include known acids and bases. Examples of acids include hydrochloric acid, phosphoric acid, nitric acid, and sulfuric acid, and examples of bases include sodium hydroxide, potassium hydroxide, lithium hydroxide, magnesium hydroxide, barium hydroxide, and calcium hydroxide.

Examples of the solvent include water-soluble organic solvents such as methanol, ethanol, acetonitrile, and acetone. It is preferable that the concentration of the solvent be such that salts and the like do not precipitate, for example, preferably 80% (v/v) or less, and a more preferable range is 0.1% (w/w) or more and 50% (w/w) or less.

Preferably, in the hemoglobin analysis method of the present invention, hemoglobins are separated by gradient elution using the above eluent. Preferably, in the method of the present invention, the above eluent is eluent B (hereinafter, referred to as solution B or simply B), and another eluent is eluent A (hereinafter, referred to as solution A or simply A), and a gradient is applied between solution A and solution B so that the proportion of solution B is increased gradually.

The eluent A may contain a buffer containing a known salt compound. Examples of buffers that can be contained in the eluent A include buffer solutions containing an organic acid or an inorganic acid. Examples of organic acids include citric acid, succinic acid, tartaric acid, malic acid, and salts thereof, and examples of inorganic acids include hydrochloric acid, nitric acid, sulfuric acid, phosphoric acid, boric acid, acetic acid, perchloric acid, and salts thereof. The buffer solution used for the eluent A can contain any one of these organic acids and inorganic acids or a combination of two or more thereof. Among these, a buffer solution containing a phosphate salt, a succinate salt, or a perchlorate salt is preferable. Examples of phosphate salts include a sodium salt and a potassium salt, with monosodium phosphate and disodium phosphate being preferable. Examples of succinate salts include a sodium salt and a potassium salt, with monosodium succinate and disodium succinate being preferable. Examples of perchlorate salts include sodium perchlorate. These phosphate salts, succinate salts and perchlorate salts may be used alone, or two or more of them may be used in combination.

The eluent A may contain, in addition to the buffer described above, a solvent and additives (for example, a hemoglobin denaturing agent, a binding agent to trivalent heme iron, a pH adjuster, a surfactant, and the like as described above) similar to those that can be contained in the eluent B as described above.

The pH of the eluent A is preferably 5.0 or more, more preferably 5.2 or more, and preferably 6.0 or less, more preferably 5.8 or less. The pH range of the eluent A is preferably 5.0 to 6.0, more preferably 5.2 to 5.8. Moreover, the osmotic pressure of the eluent A is preferably 130 mOsm/kg or more, more preferably 150 mOsm/kg or more, and preferably 210 mOsm/kg or less, more preferably 190 mOsm/kg or less. The range of the osmotic pressure of the eluent A is preferably 130 to 210 mOsm/kg, more preferably 150 to 190 mOsm/kg. In a preferable embodiment, the eluent A has a pH of 5.0 to 6.0 and an osmotic pressure of 130 to 210 mOsm/kg, more preferably 150 to 190 mOsm/kg. In a more preferable embodiment, the eluent A has a pH of 5.2 to 5.8 and an osmotic pressure of 130 to 210 mOsm/kg, more preferably 150 to 190 mOsm/kg.

Preferably, in the gradient elution in the method of the present invention, first, 100% of solution A (0% of solution B) is passed, then a gradient is applied to increase the proportion of solution B, and the proportion of solution B is increased to 100%. The range of gradient conditions may be appropriately adjusted according to the performance and the like of the column, and is not particularly limited. One example of the gradient is as follows: A:B=100:0→the proportion of B is increased to 50 to 98 volume % (preferably 70 to 95 volume %)→the proportion of B is gradually further increased→A:B=0:100. Another example of the gradient is as follows: A:B=100:0→the proportion of B is increased so that the eluent has overall a pH of 6.5 to 8.0 and an osmotic pressure of 20 to 100 mOsm/kg→the proportion of B is gradually further increased→A:B=0:100. If necessary, a time for passing a solution with A:B=100:0 again may follow.

In one embodiment, the hemoglobin analysis method of the present invention is used for the detection of abnormal hemoglobin. Examples of the abnormal hemoglobin detected by the method of the present invention includes at least one selected from the group consisting of HbS, HbC, HbE, HbD, and HbO-Arab, and the abnormal hemoglobin is preferably at least one selected from the group consisting of HbC and HbS. In the method of the present invention, each of all the abnormal hemoglobins mentioned above can be separated and detected by a single analysis.

In another embodiment, the hemoglobin analysis method of the present invention is used for the detection of thalassemia markers. Examples of the thalassemia markers detected by the method of the present invention include at least one selected from the group consisting of HbA2, HbF, HbH, Hb Bart', and Hb Constant Spring, and the thalassemia maker is preferably HbA2. In the method of the present invention, each of all the thalassemia markers mentioned above can be separated and detected by a single analysis.

Furthermore, in the hemoglobin analysis method of the present invention, both the abnormal hemoglobins and the thalassemia markers mentioned above can be detected. Furthermore, as well as detecting the abnormal hemoglobins and/or thalassemia markers, HbA0 or glycated hemoglobin HbA1c can also be detected. Therefore, the presence or absence of abnormal hemoglobins and thalassemia markers in a sample can be analyzed at once by the hemoglobin analysis method of the present invention, and the presence or absence of abnormal hemoglobins, thalassemia markers, and HbA1c in a sample can also be analyzed at once. Therefore, the method of the present invention allows to detect various types of hemoglobin by a single analysis, and thereby enables simple and rapid diagnosis of hemoglobinopathy and thalassemia.

EXAMPLES

Hereafter, the present invention is described in detail with examples, but the present invention is not limited to the following examples.

Reference Example 1: Preparation of Column for Hemoglobin Separation 1.0 g of benzoyl peroxide (manufactured by Nacalai Tesque, Inc.) was dissolved as a polymerization initiator in a monomer mixture obtained by mixing 200 g of tetraethylene glycol monomethacrylate (manufactured by NOF Corporation) as a non-crosslinkable hydrophilic acrylic monomer and 200 g of polyethylene glycol diglycidyl ether (manufactured by NOF Corporation) as a polyglycidyl ether. The obtained mixture was dispersed in 5 L of a 4 weight % aqueous solution of polyvinyl alcohol ("Gohsenol GH-20", manufactured by Nippon Synthetic Chemical Industry Co., Ltd.), heated to 80° C. under a nitrogen atmosphere while stirring, and polymerized for 1 hour. After the temperature was cooled to 30° C., 100 g of 2-methacrylamido-2-methylpropanesulfonic acid (manufactured by Toagosei Co., Ltd.) was added to the reaction system as an acrylic monomer having a cation exchange group, and a polymerization reaction was performed for 1 hour by heating again to 80° C. The obtained crosslinked polymer particles were washed with ion exchange water and acetone to obtain crosslinked polymer particles into which sulfonic acid groups have been introduced. The obtained column filler for hemoglobin separation was packed in a stainless steel column having an inner diameter of 4 mm and a length of 20 mm to prepare a cation exchange column for hemoglobin separation.

Reference Example 2: Specimen Preparation

Specimen A: The specimen was prepared by appropriately diluting a blood specimen collected from a healthy subject with a phosphate buffer solution (pH 7.00) containing 0.1% Triton X-100.

Specimen B: The specimen was prepared by appropriately diluting Lyphocheck (registered trademark) Hemoglobin A2 Control Level 2 (manufactured by Bio-Rad, containing HbA0, HbA2 and HbS) with a phosphate buffer solution (pH 7.00) containing 0.1° Triton X-100.

Specimen C: The specimen was prepared by appropriately diluting AFSC hemocontrol (manufactured by Helena Laboratories, containing HbA0, HbS and HbC) with a phosphate buffer solution (pH 7.00) containing 0.1% Triton X-100.

Specimen D: The specimen was prepared by appropriately diluting Hemoglobin A2 (manufactured by Sigma Aldrich, containing HbA2) with a phosphate buffer solution (pH 7.00) containing 0.1% Triton X-100.

Test 1

A hemoglobin analysis was performed on the specimens A to C prepared in Reference Example 2. The analysis conditions are shown below.

HPLC device: Prominence 20A series (manufactured by Shimadzu Corporation)

Detector: SPD-M20A (manufactured by Shimadzu Corporation)

Feeding pump: LC-20AD (manufactured by Shimadzu Corporation)

Deaeration unit: DGU-20A5R (manufactured by Shimadzu Corporation)

Column oven: CTO-20AC (manufactured by Shimadzu Corporation)

Autosampler: SIL-20AC (manufactured by Shimadzu Corporation)

Column: Cation exchange column for hemoglobin separation prepared in Reference Example 1

Flow rate: 1.1 mL/min

Detection wavelength: 415 nm

Sample injection volume: 10 μL

Eluents

Eluent A: buffer solution containing 40 mmol/L of sodium succinate, 45 mmol/L of sodium perchlorate, and 1 mmol/L of sodium azide (pH 5.3, osmotic pressure: 170 mOsm/kg)

Eluent B: Eluents B1 to B6 (Table 1)

Gradient: as shown in Table 2 pH meter: F-52 (manufactured by Horiba, Ltd.)

Osmometer: Osmometer 3250 (manufactured by Advanced Instruments)

TABLE 2

| Measurement Time (min) | Gradient Eluent B Concentration (volume %) | | |
|---|---|---|---|
| | Examples 1-4 | Example 5 | Example 6 |
| 0 | 0 | 0 | 0 |
| 0.99 | 0 | 0 | 0 |
| 1 | 72.5 | 86.0 | 92.5 |
| 4.5 | 77.5 | 91.0 | 97.5 |
| 5.17 | 100 | 100 | 100 |
| 5.5 | 100 | 100 | 100 |
| 5.51 | 0 | 0 | 0 |
| 6 | 0 | 0 | 0 |

Figure 1:
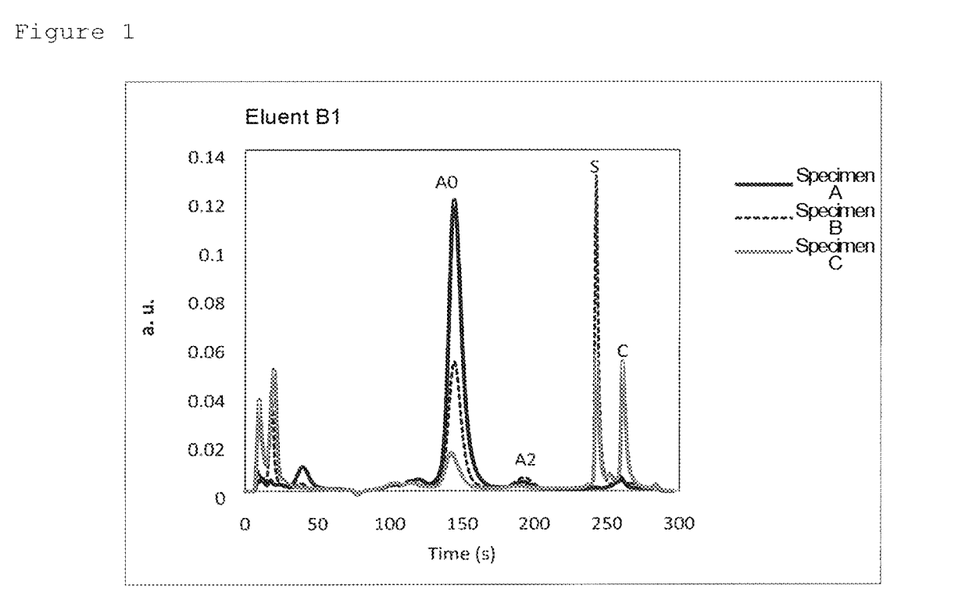
FIG. 1 Results of analysis of HbA0, HbA2, HbS and HbC in Example 1 by cation exchange chromatography using an eluent containing TES.
Figure 2:
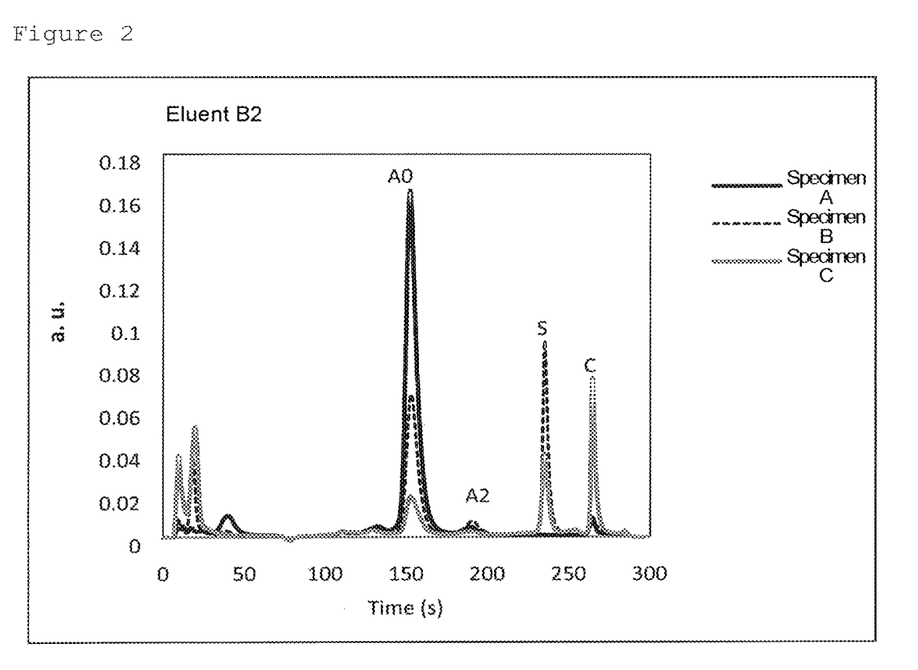
FIG. 2 Results of analysis of HbA0, HbA2, HbS and HbC in Example 2 by cation exchange chromatography using an eluent containing Tricine.
Figure 3:
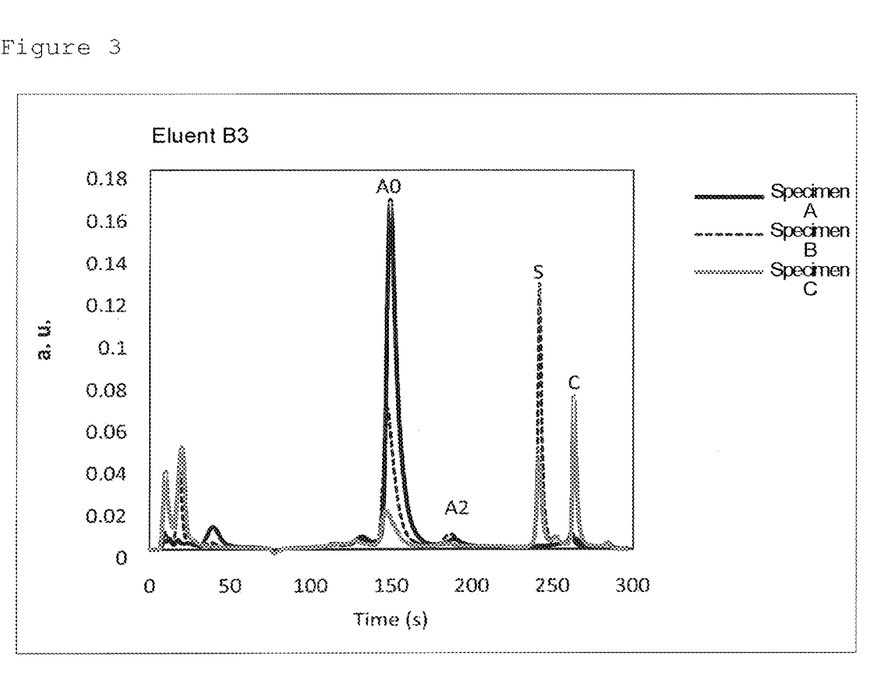
FIG. 3 Results of analysis of HbA0, HbA2, HbS and HbC in Example 3 by cation exchange chromatography using an eluent containing Bicine.
Figure 4:
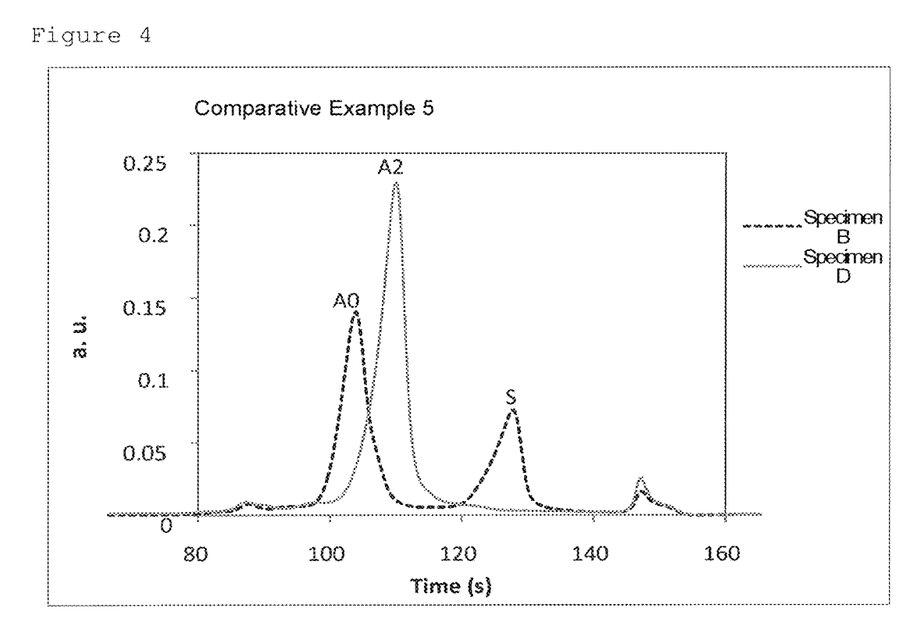
FIG. 4 Results of analysis of HbA0, HbA2, and HbS in Comparative Example 5.
Figure 5:
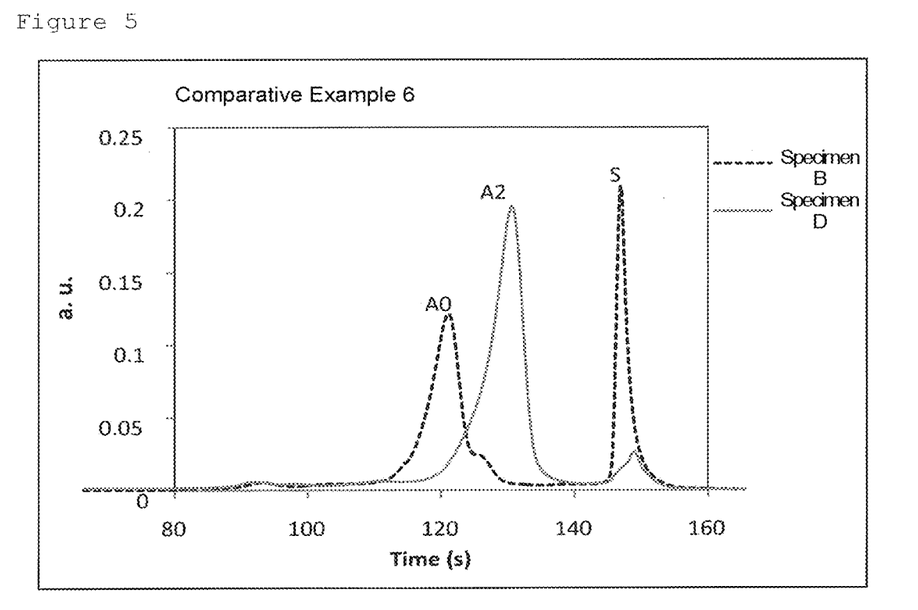
FIG. 5 Results of analysis of HbA0, HbA2, and HbS in Comparative Example 6.
Figure 6:
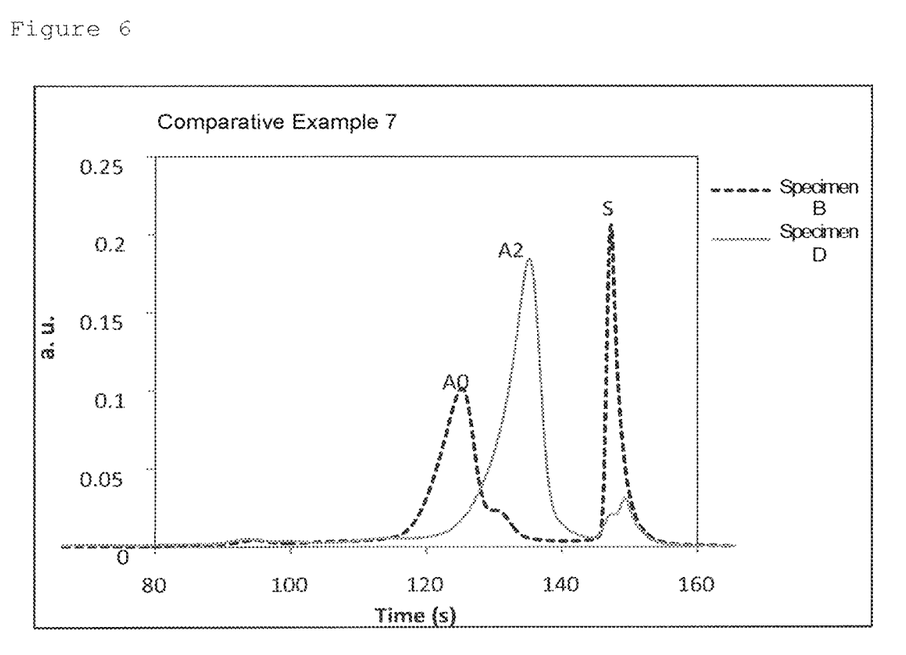
FIG. 6 Results of analysis of HbA0, HbA2, and HbS in Comparative Example 7.
Figure 7:
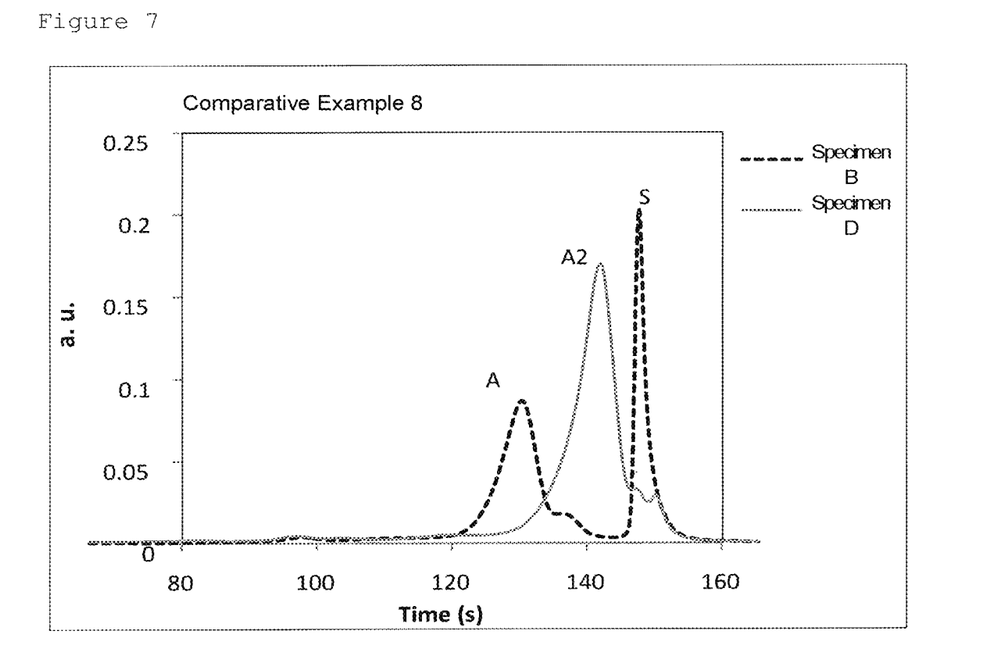
FIG. 7 Results of analysis of HbA0, HbA2, and HbS in Comparative Example 8.

The results of analysis for the specimens A to C in Examples 1 to 6 are shown in Table 3. The chromatograms of the specimens A to C obtained in Examples 1, 2, and 3 are shown in FIGS. 1, 2, and 3, respectively. In Examples 1 to 6, HbA0, HbA2, HbS, and HbC were each detected as a separate peak. The present results indicate that HbA0, HbA2, HbS, and HbC can be detected by using an eluent containing the buffer TES, Tricine or Bicine.

TABLE 3

| | Example 1 | Example 2 | Example 3 | Example 4 | Example 5 | Example 6 |
|---|---|---|---|---|---|---|
| Eluent B | B1 | B2 | B3 | B4 | B5 | B6 |
| Detection | | | | | | |
| HbA0 (specimens A, B, C) | + | + | + | + | + | + |
| HbA2 (specimens A, B) | + | + | + | + | + | + |
| HbS (specimens B, C) | + | + | + | + | + | + |
| HbC (specimen C) | + | + | + | + | + | + |

+ Peak detected,
− No peak detected

TABLE 1

| Eluent B Composition (mmol/L) | Example 1 B1 | Example 2 B2 | Example 3 B3 |
|---|---|---|---|
| TES | 10 | — | — |
| Tricine | — | 10 | — |
| Bicine | — | — | 10 |
| Sodium Nitrite | 5.0 | 5.0 | 5.0 |
| Sodium Azide | 1.0 | 1.0 | 1.0 |
| pH* | 8.4 | 8.4 | 8.4 |
| Osmotic Pressure (mOsm/kg) | 31 | 25 | 24 |

| Eluent B Composition (mmol/L) | Example 4 B4 | Example 5 B5 | Example 6 B6 |
|---|---|---|---|
| TES | 10 | 5.0 | 2.5 |
| Sodium Nitrite | 5.0 | 5.0 | 5.0 |
| Sodium Azide | 1.0 | 1.0 | 1.0 |
| pH* | 8.5 | 8.5 | 8.5 |
| Osmotic Pressure (mOsm/kg) | 31 | 23 | 19 |

*Adjusted with a 1N sodium hydroxide aqueous solution

Test 2

A hemoglobin analysis was performed on the specimens A to C prepared in Reference Example 2. The conditions other than the eluent B and the gradient conditions were the same as in Test 1. As the eluent B, the eluents described in Tables 4 to 6 were used. For the gradient conditions, the mixing ratio of the eluent A and the eluent B was appropriately determined so that HbA0 be eluted in 2.1 min. In order to confirm the elution of HbC, the time when the eluent B concentration was 100% was appropriately extended.

The results of analysis are shown in Tables 4 to 6. As shown in Table 6, HbC was not detected in Comparative Examples 1 to 3 using the eluents B having a pH of 8.0. In Comparative Examples 3 and 4 using the eluents B having an osmotic pressure exceeding 40 mOsm/kg, HbA2 overlapped the peak shoulder of HbA0, and both peaks were not sufficiently separated. In contrast, as shown in Tables 4 and 5, in Examples 7 to 18 in which the pH was higher than 8.0 and the osmotic pressure was 40 mOsm/kg or less, HbA0, HbA2, HbS and HbC were each detected. However, in Examples 10 and 11, the elution of HbA2 was slightly faster, and the peaks of HbA0 and HbA2 tended to be close to each other (data not shown). These results indicate that the eluents B having a pH of 8.1 or more and an osmotic pressure of 40 mOsm/kg or less are suitable for the analysis of various hemoglobins.

TABLE 4

|  | Example 7 | Example 8 | Example 9 | Example 10 | Example 11 | Example 12 |
|---|---|---|---|---|---|---|
| Eluent B | B7 | B8 | B9 | B10 | B11 | B12 |
| Composition (mmol/L) | | | | | | |
| TES | 2.5 | 5 | 10 | 15 | 17 | 10 |
| Sodium Nitrite | 5.0 | 5.0 | 5.0 | 5.0 | 5.0 | 5.0 |
| Sodium Azide | 1.0 | 1.0 | 1.0 | 1.0 | 1.0 | 1.0 |
| Tween 20 (%, w/w) | 0.05 | 0.05 | 0.05 | 0.05 | 0.05 | 0.05 |
| pH* | 8.2 | 8.2 | 8.2 | 8.2 | 8.2 | 8.5 |
| Osmotic Pressure (mOsm/kg) | 15 | 20 | 29 | 37 | 40 | 32 |
| Detection | | | | | | |
| HbA0 (specimens A, B, C) | + | + | + | + | + | + |
| HbA2 (specimens A, B) | + | + | + | + | + | + |
| HbS (specimens B, C) | + | + | + | + | + | + |
| HbC (specimen C) | + | + | + | + | + | + |

*Adjusted with a 1N sodium hydroxide aqueous solution

+ Peak detected,

− No peak detected

TABLE 5

|  | Example 13 | Example 14 | Example 15 | Example 16 | Example 17 | Example 18 |
|---|---|---|---|---|---|---|
| Eluent B | B13 | B14 | B15 | B16 | B17 | B18 |
| Composition (mmol/L) | | | | | | |
| Tricine | 10 | 10 | 10 | – | – | – |
| Bicine | – | – | – | 10 | 10 | 10 |
| Sodium Nitrite | 5.0 | 5.0 | 5.0 | 5.0 | 5.0 | 5.0 |
| Sodium Azide | 1.0 | 1.0 | 1.0 | 1.0 | 1.0 | 1.0 |
| Tween 20 (%, w/w) | 0.05 | 0.05 | 0.05 | 0.05 | 0.05 | 0.05 |
| pH* | 8.2 | 8.4 | 8.6 | 8.2 | 8.4 | 8.6 |
| Osmotic Pressure (mOsm/kg) | 26 | 27 | 28 | 25 | 26 | 27 |
| Detection | | | | | | |
| HbA0 (specimens A, B, C) | + | + | + | + | + | + |
| HbA2 (specimens A, B) | + | + | + | + | + | + |
| HbS (specimens B, C) | + | + | + | + | + | + |
| HbC (specimen C) | + | + | + | + | + | + |

*Adjusted with a 1N sodium hydroxide aqueous solution

+ Peak detected,

− No peak detected

TABLE 6

|  | Comparative Example 1 | Comparative Example 2 | Comparative Example 3 | Comparative Example 4 |
|---|---|---|---|---|
| Eluent B | B0-1 | B0-2 | B0-3 | B0-4 |
| Composition (mmol/L) | | | | |
| TES | 10 | 15 | 20 | 20 |
| Sodium Nitrite | 5.0 | 5.0 | 5.0 | 5.0 |
| Sodium Azide | 1.0 | 1.0 | 1.0 | 1.0 |
| Tween 20 (%, w/w) | 0.05 | 0.05 | 0.05 | 0.05 |
| pH* | 8.0 | 8.0 | 8.0 | 8.2 |
| Osmotic Pressure (mOsm/kg) | 27 | 36 | 44 | 46 |
| Detection | | | | |
| HbA0 (specimens A, B, C) | + | + | Insufficient separation of A0 and A2 | |
| HbA2 (specimens A, B) | + | + | | |
| HbS (specimens B, C) | + | + | + | + |
| HbC (specimen C) | – | – | – | + |

*Adjusted with a 1N sodium hydroxide aqueous solution

+ Peak detected,

− No peak detected

Test 3

A hemoglobin analysis was performed on the specimen B and the specimen D prepared in Reference Example 2. The analysis conditions other than the gradient and the eluent B were the same as in Test 1. As the eluent B, eluents containing a buffer solution containing sodium phosphate and sodium perchlorate having the pH and osmotic pressures described in Table 7 were used. The composition of the eluents described in Table 7 was based on the composition of an eluent containing a phosphate buffer solution generally used in conventional hemoglobin analysis. The gradient conditions were as shown in Table 8.

The results of analysis are shown in Table 7. The chromatograms of Comparative Examples 5 to 8 are shown in FIGS. 4 to 7. Specimen B contained about 5 to 7 mass % of HbA2, but in Comparative Examples 5 to 8, the peak of HbA0 and the peak of HbA2 overlapped, and both peaks were not sufficiently separated. These results indicate that HbA0 and HbA2 could not be sufficiently detected with a conventionally used eluent having a pH of 8.0 or less and an osmotic pressure of 130 mOsm/kg or more.

Test 4

A hemoglobin analysis was performed on the specimens A to C prepared in Reference Example 2, using the eluents B containing a phosphate buffer solution as described in Table 9. The conditions other than the eluent B were the same as in Test 2. As the eluent B, the eluents containing a phosphate buffer solution as described in Table 9 were used.

The results of analysis are shown in Table 9. In Comparative Examples 9 and 10, the separation between the peaks of HbA0 and HbA2 was not sufficient, and one or both of HbS and HbC were not detected. In Comparative Examples 11 to 14, HbS and HbC were detected, but the separation between the peaks of HbA0 and HbA2 was not sufficient. The eluents B of Comparative Examples 9 to 14 had a higher osmotic pressure and a higher or lower pH than the eluents of the Examples described above, and the conditions of a pH of 8.0 or more and an osmotic pressure of 40 mOsm/kg or less could not be achieved. This was thought to have led to insufficient hemoglobin detection in Comparative Examples 9 to 14.

TABLE 7

| Eluent B | Comparative Example 5 B0-5 | Comparative Example 6 B0-6 | Comparative Example 7 B0-7 | Comparative Example 8 B0-8 |
|---|---|---|---|---|
| Composition (mmol/L) | | | | |
| Sodium Phosphate | 45 | 45 | 45 | 45 |
| Sodium Perchlorate | 100 | 20 | 10 | 0 |
| Sodium Nitrite | 10 | 10 | 10 | 10 |
| Sodium Azide | 10 | 10 | 10 | 10 |
| pH* | 7.7 | 7.7 | 7.7 | 7.7 |
| Osmotic Pressure (mOsm/kg) | 330 | 170 | 150 | 130 |
| Detection | | | | |
| HbA0 (specimen B) HbA2 (specimens B and D) | Insufficient separation of A0 and A2 | | | |
| HbS (specimen B) | + | + | + | + |

*Adjusted with a 1N sodium hydroxide aqueous solution
+ Peak detected,
− No peak detected

TABLE 8

| Gradient | |
|---|---|
| Measurement Time (min) | Eluent B Concentration (volume %) |
| 0 | 0 |
| 0.98 | 0 |
| 1 | 10 |
| 2.15 | 30 |
| 2.17 | 100 |
| 2.25 | 100 |
| 2.27 | 0 |
| 2.77 | 0 |

TABLE 9

| | Comparative Example 9 | Comparative Example 10 | Comparative Example 11 | Comparative Example 12 | Comparative Example 13 | Comparative Example 14 |
|---|---|---|---|---|---|---|
| Eluent B | B0-9 | B0-10 | B0-11 | B0-12 | B0-13 | B0-14 |
| Composition (mmol/L) | | | | | | |
| Sodium Phosphate | 20 | 20 | 10 | 20 | 20 | 20 |
| Sodium Nitrite | 5.0 | 5.0 | 5.0 | 5.0 | 5.0 | 5.0 |

TABLE 9-continued

|  | Comparative Example 9 | Comparative Example 10 | Comparative Example 11 | Comparative Example 12 | Comparative Example 13 | Comparative Example 14 |
|---|---|---|---|---|---|---|
| Sodium Azide | 1.0 | 1.0 | 1.0 | 1.0 | 1.0 | 1.0 |
| Tween 20 (%, w/w) | 0.05 | 0.05 | 0.05 | 0.05 | 0.05 | 0.05 |
| pH* | 6.8 | 7.4 | 8.2 | 8.2 | 8.6 | 9.2 |
| Osmotic Pressure (mOsm/kg) | 75 | 77 | 41 | 81 | 82 | 81 |
| Detection |  |  |  |  |  |  |
| Hb0 (specimens A, B, C) | Insufficient separation of A0 and A2 | | | | | |
| HbA2 (specimens A, B) |  |  |  |  |  |  |
| HbS (specimens B, C) | − | + | + | + | + | + |
| HbC (specimen C) | − | − | + | + | + | + |

*Adjusted with a 1N sodium hydroxide aqueous solution
+ Peak detected,
− No peak detected Test 5

A hemoglobin analysis was performed on the specimens A to C prepared in Reference Example 2. The conditions other than the eluent B and the gradient conditions were the same as in Test 1. As the eluent B, the eluents described in Table 10 were used. The gradient conditions were as shown in Table 11. The results of analysis are shown in Table 10. In both Examples 19 and 20, HbA0, HbA2, HbS and HbC could be detected, as the peaks of HbA0 and HbA2 were well separated, and the peaks of HbS and HbC were also well separated.

TABLE 10

| Eluent B | Example 19 B19 | Example 20 B20 |
|---|---|---|
| Composition (mmol/L) |  |  |
| TES | 5.0 | 5.0 |
| Sodium Nitrite | 5.0 | 2.5 |
| Sodium Azide | 1.0 | 1.0 |
| pH* | 8.5 | 8.5 |
| Osmotic Pressure (mOsm/kg) | 23 | 18 |
| Detection |  |  |
| HbA0 (specimens A, B, C) | + | + |
| HbA2 (specimens A, B) | + | + |
| HbS (specimens B, C) | + | + |
| HbC (specimen C) | + | + |

*Adjusted with a 1N sodium hydroxide aqueous solution
+ Peak detected,
− No peak detected

TABLE 11

| | Gradient | |
|---|---|---|
| Measurement | Eluent B Concentration (volume %) | |
| Time (min) | Example 19 | Example 20 |
| 0 | 0 | 0 |
| 0.99 | 0 | 0 |
| 1 | 86.0 | 84.7 |
| 4.5 | 91.0 | 89.7 |
| 5.17 | 100 | 100 |
| 5.5 | 100 | 100 |
| 5.51 | 0 | 0 |
| 6 | 0 | 0 |

The invention claimed is:

1. A method for detecting the presence of at least one abnormality comprising an abnormality selected from an abnormal hemoglobin and a thalassemia marker in a hemoglobin sample, the method comprising:
   introducing a hemoglobin sample comprising hemoglobins into a cation exchange liquid chromatography column;
   gradient eluting hemoglobins from the column using an eluent A having a pH of from about 5.0 to 6.0, and an osmotic pressure of from 130 to 210 mOsm/kg and an eluent B comprising a buffer selected from the group consisting of Bicine, Tricine, and TES; and eluent B having a pH of 8.1 or more and an osmotic pressure of from 15 mOsm/kg to 40 mOsm/kg;
   comprising first introducing eluent A into the column followed by eluent B with increasing the ratio of eluent B to A until the ratio of eluent B to A is 100:0 to separate at least one hemoglobin selected from the group consisting of abnormal hemoglobins and thalassemia markers from normal hemoglobin HbA0; and
   detecting the presence or absence of abnormal hemoglobins and thalassemia markers in the eluent, wherein the abnormal hemoglobins comprise HbS and HbC, and the thalassemia markers comprise HbA2.

2. The method according to claim 1, wherein a concentration of the buffer in the eluent B is 2 to 17 mmol/L.

3. The method according to claim 1, wherein the eluent B comprises a hemoglobin denaturing agent.

4. The method according to claim 1, wherein at least one abnormal hemoglobin selected from the group consisting of HbS and HbC is separated from the HbA0 in the hemoglobin sample.

5. The method according to claim 1, wherein the thalassemia marker HbA2 is separated from HbA0 in the hemoglobin sample.

6. The method according to claim 1, wherein the cation exchange liquid chromatography column is a cation exchange high performance liquid chromatography column.

7. The method of claim 1 wherein the abnormal hemoglobins comprise HbS, HbC, HbE, and HbO-Arab.

8. The method of claim 1 wherein the thalassemia markers comprise HbA2, HbF, HbH, Hb Bart' and Hb Constant Spring.

9. The method of claim 1 wherein the method further comprises detecting the presence or absence of HbA0.

10. The method of claim 1 wherein the hemoglobin sample is derived from human blood.

* * * * *